United States Patent [19]
Oshima et al.

[11] Patent Number: 5,162,220
[45] Date of Patent: Nov. 10, 1992

[54] KEX2 ENDOPROTEASE WITHOUT A C-TERMINAL HYDROPHOBIC REGION

[75] Inventors: Takehiro Oshima, Gunma; Kensaku Mizuno, Miyazaki, both of Japan

[73] Assignees: Suntory Limited, Osaka; Hisayuki Matsuo, Miyazaki, both of Japan

[21] Appl. No.: 304,211

[22] Filed: Jan. 31, 1989

[30] Foreign Application Priority Data

Feb. 3, 1988 [JP] Japan .................... 63-021866

[51] Int. Cl.$^5$ .............. C12N 9/60; C12N 15/00; C12N 9/50
[52] U.S. Cl. .................... 435/224; 435/219; 435/172.3
[58] Field of Search .......... 435/219, 224, 172.3, 435/212

[56] References Cited

PUBLICATIONS

R. S. Fuller et al., Journal of Cellular Biochemistry, Supplement 12B, Jan. 30, 1988, p. 271, Abstract No. X015.

Fuller et al, "The *Saccharomyces cerevisiae KEX*2 Gene, Required For Processing Prepro-α-Factor, Encodes a Calcium-Dependent Endopeptidase That Cleaves After Lys-Arg and Arg-Arg Sequences," *Microbiology*, pp. 273-278, 1986.

Julius et al, "Isolation of the Putative Structural Gene For the Lysine-Argine-Cleaving Endopeptidase Required For Processing of Yeast Prepro-α-Factor," *Cell*, 37, pp. 1075-1089, 1984.

Wickner et al, "Two Chromosomal Genes Required For Killing Expression In Killer Strains of *Saccharomyces cerevisiae*," *Genetics*, 82, pp. 429-442, 1976.

Mizuno et al, "A Membrane-Bound, Calcium-Dependent Protease In Yeast α-Cell Cleaving On the Carboxyl Side of Paired Basic Residues," *BBRC*, 144, pp. 807-814, 1987.

Leibowitz et al, "A Chromosomal Gene Required For Killer Plasmid Expression, Mating, and Spore Maturation In *Saccharomyces cerevisiae*, " *PNAS*, 73, pp. 2061-2065, 1976.

Bathurst et al, "Yeast KEX2 Protease Has the Properties of a Human Proalbumin Converting Enzyme," *Science*, 235, pp. 348-350, 1987.

Fuller et al, "Enzymes Required For Yeast Prohormone Processing," *Ann. Rev. Physiol.*, pp. 345-362, 1988.

Thomas et al, "Yeast *KEX*2 Endopeptidase Correctly Cleaves a Neuroendocrine Prohormone In Mammalian Cells," *Science*, 241, pp. 226-230, 1988.

Mizuno et al, "Yeast *KEX*2 Gene Encodes An Endopeptidase Homologous to Subtilisin-Like Serine Protease," *BBRC*, 156, pp. 246-254, 1988.

*Primary Examiner*—Robert A. Wax
*Assistant Examiner*—Keith D. Hendricks
*Attorney, Agent, or Firm*—Burns, Doane, Swecker & Mathis

[57] ABSTRACT

A KEX2 endoprotease produced by a recombinant DNA technique, a KEX2 endoprotease shortened at the C-terminal of a native enzyme and still containing a C-terminal hydrophobic region, a soluble KEX2 endoprotease without a C-terminal hydrophobic region; DNA's coding for the above-mentioned enzymes; expression plasmids containing the DNA; hosts transformed with the plasmid; a process for production of the above-mentioned enzymes using the transformed host; and a process for production of biologically active polypeptide using the above-mentioned enzyme.

2 Claims, 16 Drawing Sheets

Fig. 1-1

```
             TGCATAATTCTGTCATAAGCCTGTTCTTTTTCCT -136
GGCTTAAACATCCCGTTTTGTAAAAGAGAAATCTATTCCACATAT -91
TTCATTCATTCGGCTACCATACTAAGGATAAACTAATCCCGTTGT -46
TTTTTGGCCTCGTCACATAATTATAAACTACTAACCCATTATCAG -1
ATGAAAGTGAGGAAATATATTACTTTATGCTTTTGGTGGGCCTTT -45
MetLysValArgLysTyrIleThrLeuCysPheTrpTrpAlaPhe
                                            15

TCAACATCCGCTCTTGTATCATCACAACAAATTCCATTGAAGGAC -90
SerThrSerAlaLeuValSerSerGlnGlnIleProLeuLysAsp
                                            30
CATACGTCACGACAGTATTTGCTGTAGAAAGCAATGAAACATTA  135
HisThrSerArgGlnTyrPheAlaValGluSerAsnGluThrLeu
                                            45
TCCCGCTTGGAGGAAATGCATCCAAATTGGAAATATGAACATGAT 180
SerArgLeuGluGluMetHisProAsnTrpLysTyrGluHisAsp
                                            60
GTTCGAGGGCTACCAAACCATTATGTTTTTTCAAAAGAGTTGCTA 225
ValArgGlyLeuProAsnHisTyrValPheSerLysGluLeuLeu
                                            75
AAATTGGGCAAAAGATCATCATTAGAAGAGTTACAGGGGGATAAC 270
LysLeuGlyLysArgSerSerLeuGluGluLeuGlnGlyAspAsn
                                            90
AACGACCACATATTATCTGTCCATGATTTATTCCCGCGTAACGAC 315
AsnAspHisIleLeuSerValHisAspLeuPheProArgAsnAsp
                                           105
CTATTTAAGAGACTACCGGTGCCTGCTCCACCAATGGACTCAAGC 360
LeuPheLysArgLeuProValProAlaProProMetAspSerSer
                                           120
TTGTTACCGGTAAAAGAAGCTGAGGATAAACTCAGCATAAATGAT 405
LeuLeuProValLysGluAlaGluAspLysLeuSerIleAsnAsp
                                           135
CCGCTTTTTGAGAGGCAGTGGCACTTGGTCAATCCAAGTTTTCCT 450
ProLeuPheGluArgGlnTrpHisLeuValAsnProSerPhePro
                                           150
GGCAGTGATATAAATGTTCTTGATCTGTGGTACAATAATATTACA 495
GlySerAspIleAsnValLeuAspLeuTrpTyrAsnAsnIleThr
                                           165
```

Fig. 1-2

```
GGCGCAGGGGTCGTGGCTGCCATTGTTGATGATGGCCTTGACTAC    540
GlyAlaGlyValValAlaAlaIleValAspAspGlyLeuAspTyr
                                            180

GAAAATGAAGACTTGAAGGATAATTTTTGCGCTGAAGGTTCTTGG    585
GluAsnGluAspLeuLysAspAsnPheCysAlaGluGlySerTrp
                                            195

GATTTCAACGACAATACCAATTTACCTAAACCAAGATTATCTGAT    630
AspPheAsnAspAsnThrAsnLeuProLysProArgLeuSerAsp
                                            210

GACTACCATGGTACGAGATGTGCAGGTGAAATAGCTGCCAAAAAA    675
AspTyrHisGlyThrArgCysAlaGlyGluIleAlaAlaLysLys
                                            225

GGTAACAATTTTTGCGGTGTCGGGGTAGGTTACAACGCTAAAATC    720
AlaAlaSerLeuIleTyrGlyLeuAspValAsnAspIleTyrSer
                                            240

TCAGGCATAAGAATCTTATCCGGTGATATCACTACGGAAGATGAA    765
SerGlyIleArgIleLeuSerGlyAspIleThrThrGluAspGlu
                                            255

GCTGCGTCCTTGATTTATGGTCTAGACGTAAACGATATATATTCA    810
AlaAlaSerLeuIleTyrGlyLeuAspValAsnAspIleTyrSer
                                            270

TGCTCATGGGGTCCCGCTGATGACGGAAGACATTTACAAGGCCCT    855
CysSerTrpGlyProAlaAspAspGlyArgHisLeuGlnGlyPro
                                            285

AGTGACCTGGTGAAAAAGGCTTTAGTAAAAGGTGTTACTGAGGGA    900
SerAspLeuValLysLysAlaLeuValLysGlyValThrGluGly
                                            300

AGAGATTCCAAAGGAGCGATTTACGTTTTTGCCAGTGGAAATGGT    945
ArgAspSerLysGlyAlaIleTyrValPheAlaSerGlyAsnGly
                                            315

GGAACTCGTGGTGATAATTGCAATTACGACGGCTATACTAATTCC    990
GlyThrArgGlyAspAsnCysAsnTyrAspGlyTyrThrAsnSer
                                            330

ATATATTCTATTACTATTGGGGCTATTGATCACAAAGATCTACAT   1035
IleTyrSerIleThrIleGlyAlaIleAspHisLysAspLeuHis
                                            345

CCTCCTTATTCCGAAGGTTGTTCCGCCGTCATGGCAGTCACGTAT   1080
ProProTyrSerGluGlyCysSerAlaValMetAlaValThrTyr
                                            360
```

Fig. 1-3

```
TCTTCAGGTTCAGGCGAATATATTCATTCGAGTGATATCAACGGC           1125
SerSerGlySerGlyGluTyrIleHisSerSerAspIleAsnGly
                                           375
AGATGCAGTAATAGCCACGGTGGAACGTCTGCGGCTGCTCCATTA           1170
ArgCysSerAsnSerHisGlyGlyThrSerAlaAlaAlaProLeu
                                           390
GCTGCCGGTGTTTACACTTTGTTACTAGAAGCCAACCCAAACCTA           1215
AlaAlaGlyValTyrThrLeuLeuLeuGluAlaAsnProAsnLeu
                                           405
ACTTGGAGAGACGTACAGTATTTATCAATCTTGTCTGCCGTAGGG           1260
ThrTrpArgAspValGlnTyrLeuSerIleLeuSerAlaValGly
                                           420
TTAGAAAAGAACGCTGACGGAGATTGGAGAGATAGCGCCATGGGG           1305
LeuGluLysAsnAlaAspGlyAspTrpArgAspSerAlaMetGly
                                           435
AAGAAATACTCTCATCGCTATGGCTTTGTTAAAATCGATGCCCAT           1350
LysLysTyrSerHisArgTyrGlyPheGlyLysIleAspAlaHis
                                           450
AAGTTAATTGAAATGTCCAAGACCTGGGAGAATGTTAACGCACAA           1395
LysLeuIleGluMetSerLysThrTrpGluAsnValAsnAlaGln
                                           465
ACCTGGTTTTACCTGCAAACATTGTATGTTTCCCAGTCCACAAAC           1440
ThrTrpPheTyrLeuProThrLeuTyrValSerGlnSerThrAsn
                                           480
TCCACGGAAGAGACATTAGAATCCGTCATAACCATATCAGAAAAA           1485
SerThrGluGluThrLeuGluSerValIleThrIleSerGluLys
                                           495
AGTCTTCAAGATGCTAACTTCAAGAGAATTGAGCAGGTCAGGGTA           1530
SerLeuGlnAspAlaAsnPheLysArgIleGluHisValThrVal
                                           510
ACTGTAGATATTGATACAGAAATTAGGGGAACTACGACTGTCGAT           1575
ThrValAspIleAspThrGluIleArgGlyThrThrThrValAsp
                                           525
TTAATATCACCAGCGGGGATAATTTCAAACCTTGGCCTTGTAAGA           1620
LeuIleSerProAlaGlyIleIleSerAsnLeuGlyValValArg
                                           540
CCAAGAGATGTTTCATCAGAGGGATTCAAAGACTGGACATTCATG           1665
ProArgAspValSerSerGluGlyPheLysAspTrpThrPheMet
                                           555
```

Fig. 1-4

```
TCTGTAGCACATTGGGGTGAGAACGGCGTAGGTGATTGGAAAATC    1710
SerValAlaHisTrpGlyGluAsnGlyValGlyAspTrpLysIle
                                           570

AAGGTTAAGACAACAGAAAATGGACACAGGATTGACTTCCACAGT    1775
LysValLysThrThrGluAsnGlyHisArgIleAspPheHisSer
                                           585

TGGAGGCTGAAGCTCTTTGGGGAATCCATTGATTCATCTAAAACA    1880
TrpArgLeuLysLeuPheGlyGluSerIleAspSerSerLysThr
                                           600

GAAACTTTCGTCTTTGGAAACGATAAAGAGGAGGTTGAACCAGCT    1845
GluThrPheValPheGlyAsnAspLysGluGluValGluProAla
                                           615

GCTACAGAAAGTACCGTATCACAATATTCTGCCAGTTCAACTTCT    1890
AlaThrGluSerThrValSerGlnTyrSerAlaSerSerThrSer
                                           630

ATTTCCATCAGCGCTACTTCTACATCTTCTATCTCAATTGGTGTG    1935
IleSerIleSerAlaThrSerThrSerSerIleSerIleGlyVal
                                           645

GAAACGTCGGCCATTCCCCAAACGACTACTGCGAGTACCGATCCT    1980
GluThrSerAlaIleProGlnThrThrThrAlaSerThrAspPro
                                           660

GATTCTGATCCAAACACTCCTAAAAAACTTTCCTCTCCTAGGCAA    2025
AspSerAspProAsnThrProLysLysLeuSerSerProArgGln
                                           675

GCCATGCATTATTTTTTAACAATATTTTTGATTGGCGCCACATTT    2670
AlaMetHisTyrPheLeuThrIlePheLeuIleGlyAlaThrPhe
                                           690

TTGGTGTTATACTTCATGTTTTTTATGAAATCAAGGAGAAGGATC    2115
LeuValLeuTyrPheMetPhePheMetLysSerArgArgArgIle
                                           705

AGAAGGTCAAGACGCGAAACGTATGAATTCGATATCATTGATACA    2160
ArgArgSerArgAlaGluThrTyrGluPheAspIleIleAspThr
                                           720

GACTCTGAGTACGATTCTACTTTGGACAATGGAACTTCCGGAATT    2205
AspSerGluTyrAspSerThrLeuAspAsnGlyThrSerGlyIle
                                           735

ACTGAGCCCGAAGAGGTTGAGGACTTCGATTTTGATTTGTCCGAT    2250
ThrGluProGluGluValGluAspPheAspPheAspLeuSerAsp
                                           750
```

Fig. 1-5

```
GAAGACCATCTTGCAAGTTTGTCTTCATCAGAAAACGGTGATGCT  2295
GluAspHisLeuAlaSerLeuSerSerSerGluAsnGlyAspAla
                                           765
GAACATACAATTGATAGTGTACTAACAAACGAAAATCCATTTAGT  2340
GluHisThrIleAspSerValLeuThrAsnGluAsnProPheSer
                                           780
GACCCTATAAAGCAAAAGTTCCCAAATGACGCCAACGCAGAATCT  2385
AspProIleLysGlnLysPheProAsnAspAlaAsnAlaGluSer
                                           795
GCTTCCAATAAATTACAAGAATTACAGCCTGATGTTCCTCCATCT  2430
AlaSerAsnLysLeuGlnGluLeuGlnProAspValProProSer
                                           810
TCCGGACCATCGTGATTCGATATGTACAGAAAGCTTCAAATTACA  2475
SerGlyArgSer
         814
AAATAGCATTTTTTTCTTATAGATTATAATACTCTCTCATACGTA  2520

TACGTATATGTGTATATGATATATAAACAAACATTAATATCCTAT  2565

TCCTTCCGTTTGAAATCCCTATGATGTACTTTGCATTGTTTGCAC  2610

CCGCGAATAAAATGAAAACTCCGAACCGATATATCAAGCACATAA  2655

AAGGGGAGGGTCCAATTAATGCATATTTAAGACCACAGCTGAATA  2700

ACTTTAAAACGGCAGACAAAACAAAAAATAGGTCGAATAAACCTT  2745

ACCTGCCTAGAAGGAATGACAGCAGCTAATAAGAATATTGTCTTC  2790

GGATTTTCCAGATCCATTAGCGCAATTCTACTAATATGCTTTTTC  2835

TTTGAAAAGTCTGCGGTGATATGGAGCATGATATGGGCATGGATG  2880

ATACTTCGGGATACACGAGGCCAGAAATGTGCAGGCTGGGTCG    2923
```

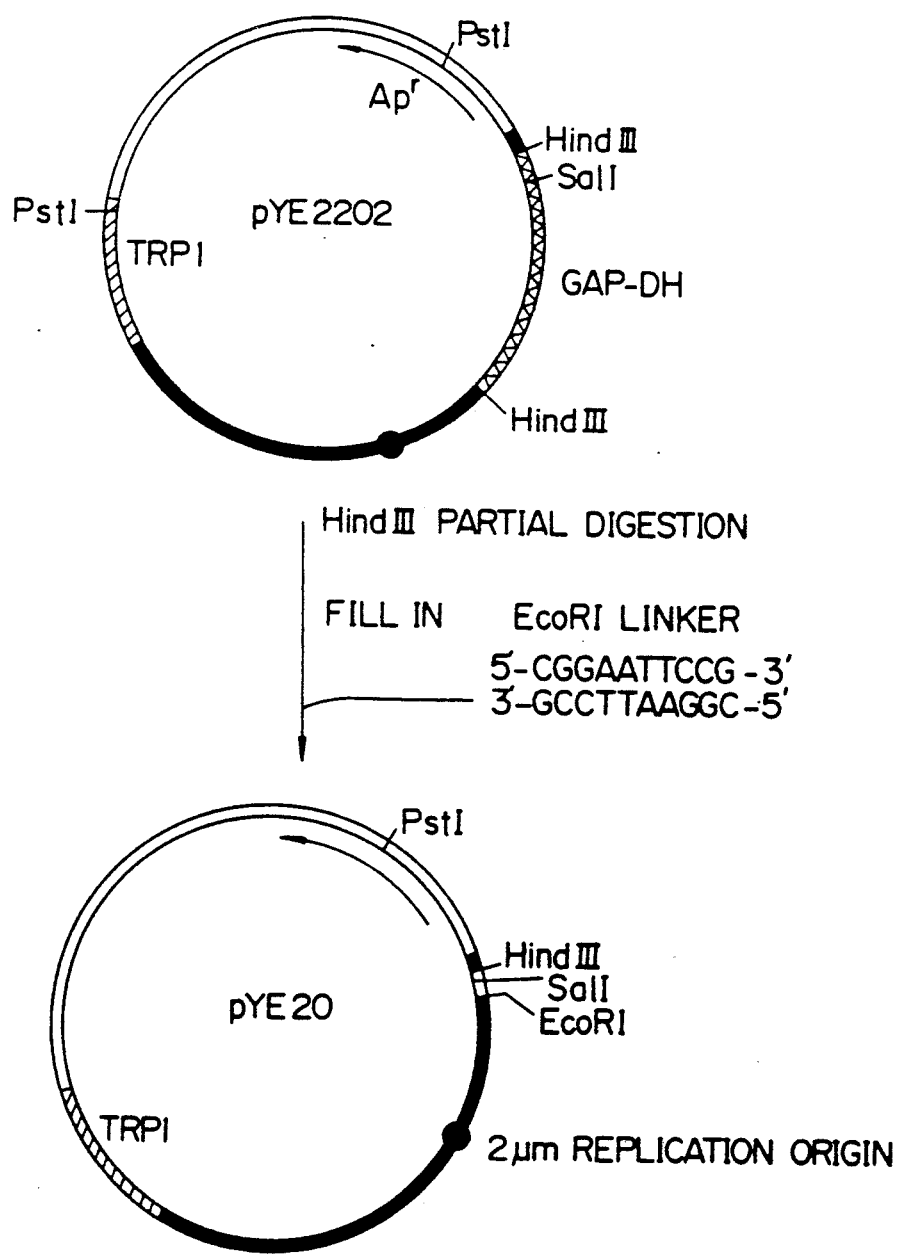

Fig.6

```
KEX2                    40             50             60             70             80             90
        YFAVESNETLSRLEEMHPNWKYEHDVRGLPNHYVFSKELLKLGKRSSLEELQGDNDHIL
SUB     MRGKKKVWISLLFALALIFTMAFGSTSSAQAGKSNGEKKYIVGFKQTMSTMSAAKKKDVI
                10            20             30             40             50             60

KEX2                   100            110            120            130            140            150
        SVHDLFPRNDLFKRLPVPAPPMDSSLLPVKEAEDKLSINDPLFERQWHLVNPSFGSDIN
SUB     SEKGGKVQKQ-EKYVDAASATLNEKAVKELKKDPSVAYVEEDHVAHAYAQSVPYGVSQLK
                70            80             90            100            110

KEX2                   160            170            180            190            200            210
        VLDLWYNNITGAGVVAAIVDDGLDYENEDLKDNFCAEGSWDFNDNTNLPKPRLSDDYHGT
SUB     APALHSQGYTGSNMKVAVIDSGIDSSHFDLKI---VAGGASMVPSEIN---PFQDNNSHGT
              120            130            140            150            160            170

KEX2                   220            230            240            250            260            270
        RCAGEIAAKKGNNFCGVGVGYNAKISGIRILSGDITTEDEAASLIYGLDVNDIIYSCSWGP
SUB     HVAGTVAALN-NSIGVLGVAPSASLYAVKVLGAD------GSGQMSWIINGIL---EMAI
              180            190            200            210            220

KEX2                   280            290            300            310            320            330
        ADDGRHLQ-GPSDLVKKALVRGVTEGRDSKGAIYVFASGNGTRGDNCNYDGYTNSIYS-
SUB     ANNMDVINMSLGGPSGSAALKAAVDKAVASGVVVAAAGNEGTSGSSST-VGYPGKYFSV
              230            240            250            260            270            280

KEX2                   340            350            360            370            380            390
        ITIGAIDHKDLHPPYSEGCSAVMAVTYSSGSGEYTIHSSDINGRCSNSHGGTSAAAPLAAG
SUB     VYTLLEANPNLTMRDMQYLSILSAVGLEKNADGDWRDSAMGKKYS
              290            300            310            320            330

KEX2                   400            410            420            430
        AAALILSKHPNWTNTQVRSSLENTTTKLGDSFYYGKLINVQAAAQ
SUB     
              340            350            360            370            380
```

KEX2 ENDOPROTEASE WITHOUT A C-TERMINAL HYDROPHOBIC REGION

BACKGROUND OF THE INVENTION

1. Field of the Invention

The present invention relates to a KEX2 endoprotease produced by a recombinant DNA technique, a process for production thereof, a gene coding for the KEX2 endoprotease and used for the process, and the use of the KEX2 endoprotease.

2. Description of the Related Art

KEX2 endoprotease of Saccharomyces yeast is a protease which specifically processes a mating type factor and a killer factor. The properties of the KEX2 endoprotease are reported to be as following: (1) KEX2 cleaves a C-terminal of Lys-Arg sequence in a mating type factor, and a C-terminal of Lys-Arg sequence and Pro-Arg sequence in a killer factor; (2) a purification thereof was attempted, and it was found that the enzyme is present in a membrane fraction and requires calcium ion for activation thereof; (3) KEX2 is a glycoprotein having a molecular weight of 100 to 120 K Dalton; (4) KEX2 specifically cleaves a C-terminal of sequences Arg-Arg, Lys-Arg, and Pro-Arg (BBRC, 144, 807–814, 1987).

On the other hand, it is considered that, in animal hormones (biologically active peptides), the mature form thereof is generated from a corresponding precursor through the cleavage by a specific protease, and the structures of there cleavage sites very closely match a substrate specificity of the KEX2 endoprotease. For example, a mature form of insulin is generated by cleaving a precursor consisting of B chain-C peptide-A chain, to remove the C-peptide. Sequences Arg-Arg or Lys-Arg locates at the ends of the C-peptide (Nature, 282, 525–527, 1979). Further, a glucagon molecule also has a sequence Lys-Arg at both ends thereof (Proc. Natl. Acad. Sci. USA, 79, 345–349, 1982); a gastrin molecule has an Arg-Arg sequence at the C-terminal thereof (Pro. Natl. Acad. Sci. USA, 79, 1049–1053, 1982); somatostatin is located in the C-terminal side of the precursor thereof, and an Arg-Lys sequence precedes a mature somatostatin (Nature, 288, 137–141, 1980).

Note, when producing a desired peptide such as a peptide hormone by a recombinant DNA technique, it is sometimes difficult to directly produce the desired peptide due to an instability of the desired peptide in a host cell, and as one way of solving this problem, the desired peptide is produced as a fused protein comprising a protective (or stabilizing) protein, and the fused protein is cleaved to liberate the desired protein or peptide. To liberate the desired protein or peptide, however, the fused protein must be cleaved at a predetermined specific site, and since this specific cleavage site is similar to the cleavage site for the KEX2 endoprotease, it is considered that the KEX2 endoprotease will be useful for cleavage of the fused protein to liberate the desired protein or peptide.

Nevertheless, since the KEX2 endoprotease is recovered from Saccharomyces yeast in a membrane fraction and must be solubilized by a surfactant for purification, problems arise in the industrial production thereof. To solve these problems, a gene engineering technology can be advantageously utilized, and if an enzyme which is soluble exhibits the same substrate specificity as that of the native KEX2 endoprotease, this is even more advantageous.

SUMMARY OF THE INVENTION

Accordingly, the present invention provides a KEX2 endoprotease produced by a recombinant DNA technique and a soluble protein exhibiting a KEX2 endoprotease activity (hereinafter designated as a soluble KEX2 endoprotease), genes coding for these enzymes, and a process for the production thereof applicable as an industrial process.

More specifically, the present invention provides a KEX2 endoprotease produced by a recombinant DNA technique.

The present invention also provides a KEX2 endoprotease shortened at the C-terminal of a native enzyme but still containing a C-terminal hydrophobic region.

The present invention also provides a soluble KEX2 endoprotease without a C-terminal hydrophobic region.

The present invention further provides a DNA coding for the KEX2 endoprotease.

The present invention also provides a DNA coding for a KEX2 endoprotease shortened at the C-terminal of the native enzyme but still containing a C-terminal hydrophobic region.

Moreover, the present invention provides a DNA coding for a soluble KEX2 endoprotease without a C-terminal hydrophobic region.

The present invention also provides expression plasmids containing a DNA coding for the KEX2 endoprotease.

Further, the present invention provides expression plasmids containing a DNA coding for a KEX2 endoprotease shortened at the C-terminal of a native enzyme but still containing a C-terminal hydrophobic region.

The present invention also provides expression plasmids containing a DNA coding for a soluble KEX2 endoprotease without a C-terminal hydrophobic region.

Moreover, the present invention provides a host transformed with a plasmid containing a DNA coding for the KEX2 endoprotease.

The present invention also provides a host transformed with a plasmid containing a DNA coding for the KEX2 endoprotease shortened at the C-terminal of a native enzyme but still containing a C-terminal hydrophobic region.

Moreover, the present invention provides a host transformed with a plasmid containing a DNA coding for a soluble KEX2 endoprotease without a C-terminal hydrophobic region.

The present invention further provides a process for the production of KEX2 endoprotease, characterized by culturing a host transformed with a plasmid containing a DNA coding for the KEX2 endoprotease and capable of expressing the DNA to produce the enzyme, and recovering the enzyme.

The present invention further provides a process for the production of a KEX2 endoprotease shortened at the C-terminal of a native enzyme but still containing a terminal hydrophobic region, characterized by culturing a host transformed with a plasmid containing a DNA coding for the shortened KEX2 endoprotease and capable of expressing the DNA to produce the enzyme, and recovering the enzyme.

The present invention still further provides a process for the production of a soluble KEX2 endoprotease without a C-terminal hydrophobic region, characterized by culturing a host transformed with a plasmid containing a DNA coding for the soluble KEX2 endoprotease and capable of expressing the DNA to produce the soluble enzyme, and recovering the soluble enzyme.

The present invention additionally provides a process for the production of a biologically active peptide or protein (biologically active substance), characterized in (1) acting the KEX2 endoprotease produced by recombinant DNA technology, the shortened KEX2 endoprotease or the soluble KEX2 endoprotease on a precursor or fused protein of the biologically active substance, in which the precursor or fused protein of the biologically active substance has at one end thereof or at each end thereof an amino acid sequence capable of being cleaved by the KEX2 endoprotease, in an aqueous medium, to liberate the biologically active substance; and (2) recovering the biologically active substance from the reaction mixture.

BRIEF DESCRIPTION OF THE DRAWINGS

FIGS. 2-1 to 2-2 represent a process for the construction of a plasmid pYE20;

FIG. 3 represents a process for the construction of a YCpLe vector;

FIGS. 4-1 to 4-2 represent a process for a cloning of the KEX2 gene, and a process for the construction of pUC18-KEX2(5.0);

FIG. 5A represents restriction enzyme maps of KEX-2(RI) and KEX2(5.0);

FIG. 5B represents a strategy for determination of a nucleotide sequence of DNA containing the KEX2 endoprotease gene;

FIG. 6 represents a comparison between amino acid sequences of the KEX2 endoprotease and of subtilisin, wherein the numbers are amino acid members counted from the N-terminal;

DESCRIPTION OF THE PREFERRED EMBODIMENTS

Figures 1, 2:
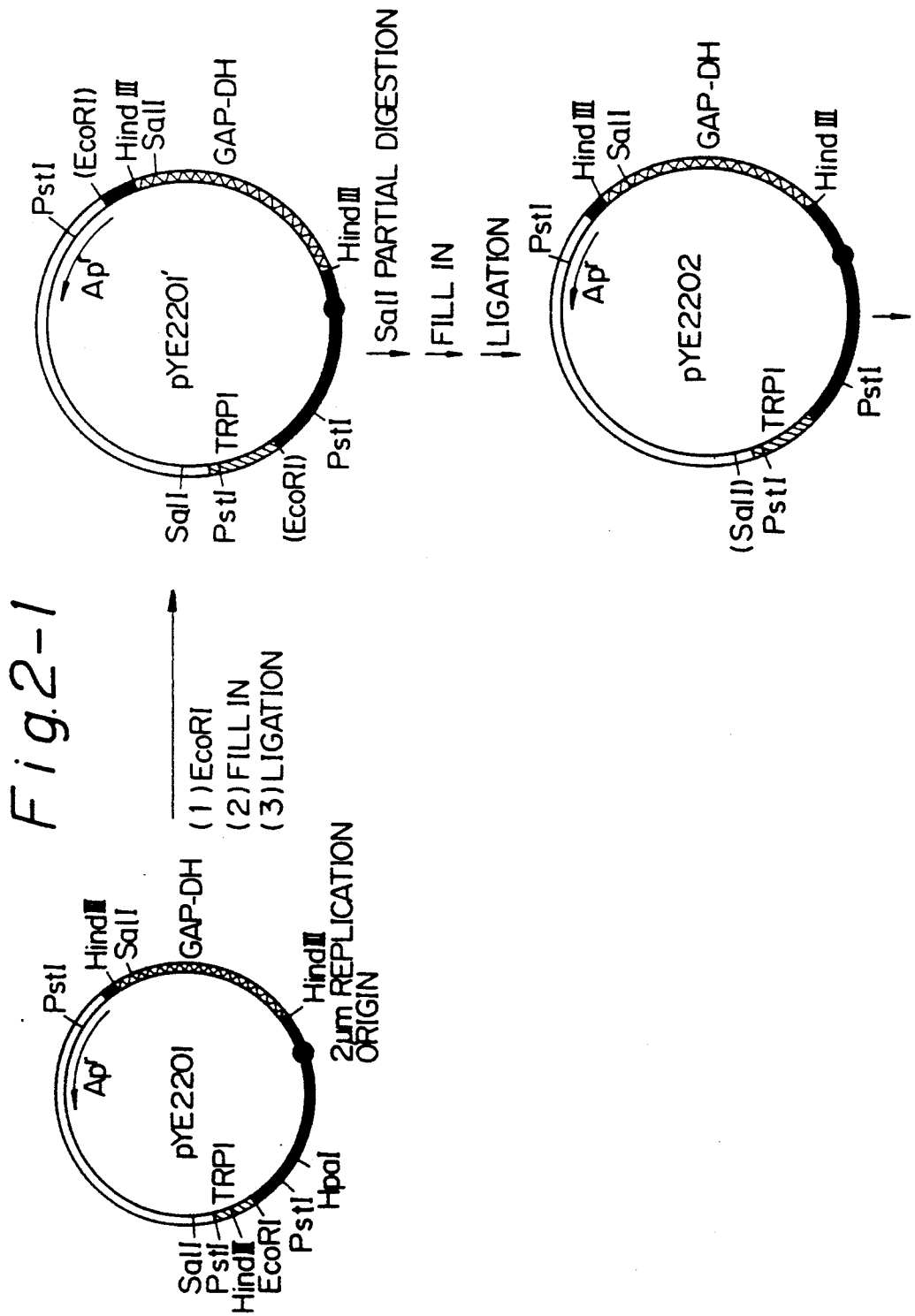
FIGS. 1-1 to 1-5 represent a nucleotide sequence of a gene coding for KEX2 endoprotease and a corresponding amino acid sequence.

The present inventors cloned a DNA coding for a KEX2 endoprotease, determined a nucleotide sequence of the DNA, expected an entire amino acid sequence of the KEX2 endoprotease on the basis of the nucleotide sequence, and found that the KEX2 endoprotease has two hydrophobic regions at the N-terminal side and C-terminal side thereof, respectively. Moreover, the present inventors, on the basis of an assumption that the C-terminal hydrophobic region is responsible for the binding thereof to a Golgi body of an yeast cell, found that the binding to the Golgi body can be prevented by deleting this hydrophobic region and the KEX2 endoprotease can be solubilized while maintaining an original substrate specificity.

Next, a process for the construction of the gene of the present invention, a process for the production of a desired enzymes, and the use thereof, are described in detail.

(1) Isolation of DNA

Although the KEX2 gene has been cloned by D. Julius, Cell, 37, 1075–1089, 1984, a report on the nucleotide sequence thereof has not been made. Accordingly to determine a structure of the KEX2 gene, first a clone complementing a kex2 mutation is cloned. Namely, a chromosomal DNA of *Saccharomyces cerevisiae* X2180-1B (MATα SUC2 mal gal2 CUP1: available from Yeast Genetic Stock Center, Berkeley College, University of California) is isolated by a method of Cryer et al., Method in Cell Biology, 2, 39–44, 1975. Next, DNA fragments capable of complementing a kex2 mutation are isolated by a method of D. Julius, supra. Namely, the chromosomal DNA from *Saccharomyces cerevisiae* X2180-2B is digested with restriction enzymes, the digested DNA fragments are separated by agar gel electrophoresis, a gel section containing desired DNA fragments is cut out, and the DNA fragments are electroeluted and recovered by ethanol precipitation.

On the other hand, a YEp type shuttle vector, such as pYE 20, containing a TRP1 gene and 2 μm replication origin, as well as an ampicillin resistant gene and a replication origin of pBR322 is cleaved with a restriction enzyme to obtain a DNA fragment. DNA fragments from chromosomal DNA of *Sacch. cerevisiae*, and the DNA fragment from the shuttle vector are mixed and ligated, using a T4 DNA ligase, and the ligation mixture is used to transform host cells such as *E. coli* DH-1. Next, separately obtained ampicillin resistant transformants are mixed, and from the mixture, plasmid DNA's are prepared by a conventional procedure to prepare an X2180-1B chromosomal DNA gene bank. This gene bank is used to transform yeast having a kex2-8 mutation, such as Sacch. cerevisiae K16-572 (MATα leu2 his3 ura3 trp1 kex2-8). From the Trp+ transformants thus obtained, transformants which complement the kex2-8 mutation, i.e., strains producing a killer factor, are selected using a killer sensitive strain such as *Sacch. cerevisiae* 5X47 (MATa/MATα his1/+ trp1/+ ura3/+; Genetics, 82, 429–442, 1976), according to Wickmer and Leibowitz, Genetics, 82, 429–442, 1976. From the transformant, i.e., killer factor-producing strain, a plasmid DNA is isolated by an SDS-alkaline method (Recombinant DNA Techniques: An Introduction ed., R. L. Rodriguez and R. C. Tait, ADDISON-WESLEY PUBLISHING CORP. Massachusetts, pp 171–172, 1983), and is used to transform host cells such as *E. coli* DH-1. From the transformant, a plasmid DNA such as pYE-KEX2(5.0) or pYE-KEX2(RI)a is isolated and used again to transform yeast cells having a kex2-8 mutation, such as *Sacch. cerevisiae* K16-57C. If the obtained Trp+ transformant is a killer factor producer, the plasmid contained in the transformant is determined to contain a DNA fragment which complements the kex2-8 mutation.

Next, the plasmid is digested with a restriction enzyme to obtain DNA fragments which are then subcloned to pUC18. The subcloned DNA fragment, which complements the kex2-8 mutation, is digested with a restriction enzyme such as NsiI, HindIII, Sau-3AI, HaeIII, XhaI, BalII, Cfr101, ClaI, TaqI, PvuII or EcoRI, and the resulting fragments are inserted into a multi-linker site of an M13mp18 or M13mp19 vector. A nucleotide sequence of the inserts is determined by a dideoxy method, Markland, F. S. and Smith, E. L., 1971, in the Enzyme, Vol. 3, ed. Boyer, P. D., Academic Press, New York, pp. 561–608, to select a plasmid coding for the KEX2 endoprotease, such as pUC18-KEX2(5.0).

(2) Analysis of DNA

Figure 5:
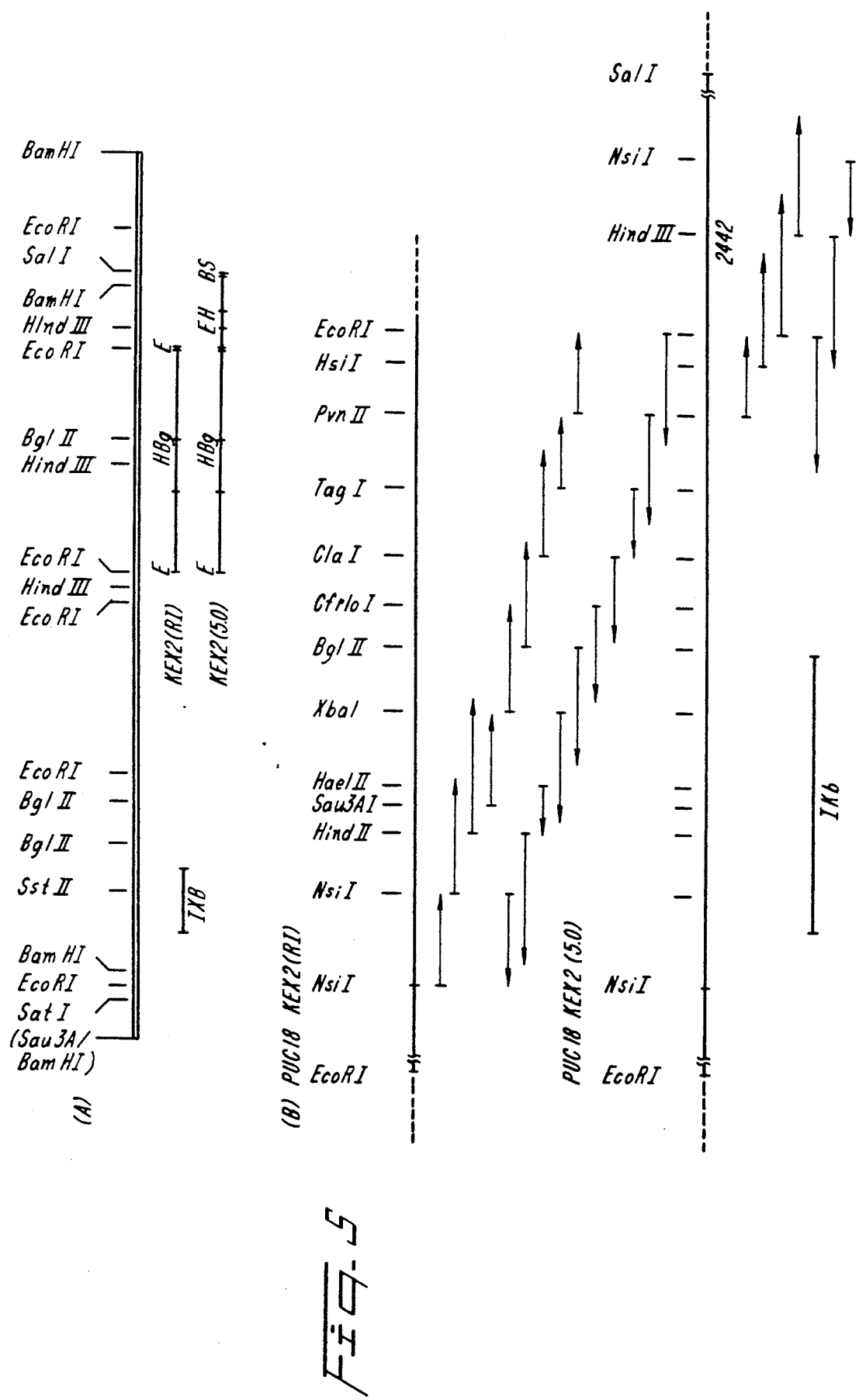

A restriction enzyme cleavage map of the cloned DNA in a plasmid such as pYE-KEX2(5.0) is constituted (see FIG. 5A). Next, to determine a nucleotide sequence of the DNA, the DNA is cleaved with various restriction enzymes and the resulting DNA fragments are subcloned into M13 phage. The insert portion of each clone is sequenced by a method of Sanger F. et al., Proc. Natl. Acad. Sci. USA, 34, 5463–5467, 1977 (see FIG. 5B), and as a result of this sequencing, the cloned DNA, for example, in pUC18-KEX2(5.0), contained a coding region coding for an 814 amino acid sequence (see FIG. 1).

Figure 7:
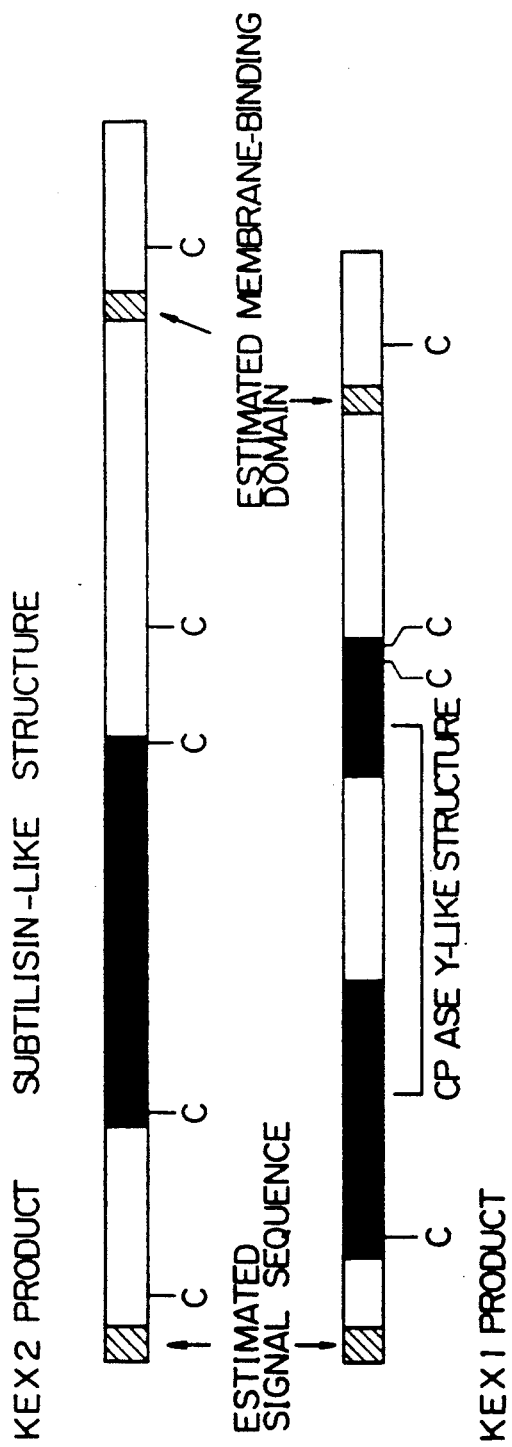
FIG. 7 represents a comparison between structures of the KEX1 product and KEX2 product, wherein the structure of the KEX1 product was taken from Cell, 50, 573-584 (1987)

An amino acid sequence expected from the nucleotide sequence is characterized as follows: (1) N-terminal portion (from first amino acid to 28th amino acid in an amino acid sequence represented in FIG. 1) and C-terminal portion (from 679th amino acid to 699th amino acid in the amino acid sequence in FIG. 1) represent regions rich in hydrophobic amino acids. (2) The amino acid sequence contains in the region thereof from the 96th amino acid to the 421th amino acid, an amino acid sequence similar to that of serine protease subtilisin (see FIG. 6). Due to this homology with subtilisin, the KEX2 endopeptidase is considered to be a serine protease. (3) The amino acid sequence is similar to that of the KEX1 carboxypeptidase (Cell, 50, 573–584, 1987), which is considered to involve processing of α-mating factor and killer factor both containing regions rich in hydrophobic amino acids near the C-terminals and N-terminals thereof. Both KEX1 and KEX2 are expected to be present in Golgi body and an N-terminal hydrophobic region is involved in passing the protein through the rough endoplasmic reticulum, and the C-terminal hydrophobic region is expected to be a membrane penetrating region necessary for a transportation to and harboring at the Golgi body (see FIG. 7).

(3) Expression of cloned DNA in host

To express a KEX2 endoprotease coded in a cloned DNA such as KEX2(5.0), expression vectors are constructed. The vectors used herein include a YEp vector having 2 μm replication origin (multicopy), and YCp vector having ARS1 and CEN4 (single copy). Next, the expression vector is used to transform host cells. Host microorganisms include *E. coli., Bacillus subtilis*, yeast and the like. Although the above-mentioned vectors are for a yeast host, an expression vector suitable for *E. coli., Bacillus subtilis* and the like can be used, depending on the host chosen. The transformation provides a host for the expression of the desired gene, such as *Sacch. cerevisiae* K16-57C/pYE-KEX2(5.0) (see FIG. 4).

Moreover, if a C-terminal hydrophobic region is responsible for harboring the protein on the Golgi body, it is expected that a protein without the C-terminal hydrophobic region is soluble and extracellularly secreted, while maintaining the biological activities of a native enzyme. Therefore, various KEX2 endoprotease, such as KEX2Δ5, without the C-terminal portion are produced.

The transformant can be cultured by a conventional procedure. For example, transformant cells are inoculated in a conventional liquid medium, and cultured with agitation and/or aeration. Where a desired enzyme accumulates in cells, cells are collected and disrupted by a conventional procedure such as sonication or French press to obtain a soluble fraction or membrane fraction containing the desired enzyme. In the latter case, the desired enzyme may be then solubilized. If the desired enzyme is extracellularly secreted, the enzyme is directly recovered from the culture supernatant.

(4) Assay of enzyme activity

The activity of the present enzyme is assayed by a method of K. Mizuno et al., BBRC, 144, 807–814, 1987. Namely, the calcium-dependent endoprotease activity is measured using Boc-Gln-Arg-Arg-MCA as a substrate.

A cloned DNA, such as KEX2(R1), coding for a protein without a C-terminal of the native enzyme can complement a kex2 mutation in both the YEp vector and YCp vector, regardless of the directions of insertion of the cloned DNA, and can express an endoprotease activity. Where a single copy vector such as a YCp vector is used, the expressed endoprotease activity is roughly the same as that provided by a wild yeast strain such as *Sacch. cerevisiae* R27-7C, and where a multi copy vector such as a pYE vector is used, the expressed endoprotease activity is higher than that provided by the wild yeast strain. Moreover, where a cloned DNA, such as KEX2(5.0), coding for an entire KEX2 endoprotease is inserted in the YEp vector, expressed activity is higher than that of the wild yeast strain. These higher activities are explained by a gene dosage effect.

Peptides without a C-terminal portion of the native enzyme, designated as soluble KEX2 endoprotease, are, as expected, extracellularly secreted and exhibit a calcium-dependant endoprotease activity. Table 2 shows an ability to complement a kex2 mutation in host cell and the enzyme activity of each soluble KEX2 endoprotease. As seen from Table 2, any protein encoded by DNA containing a coding region until the PvuII site, corresponding to an amino acid sequence from the first amino acid to 614th amino acid, can complement the kex2 mutation and exhibit the KEX2 endoprotease activity. Therefore, the hydrophobic region near the C-terminal is not essential for the activities.

Accordingly, the KEX2 endoprotease of the present invention includes, in addition to the full length or native enzyme, any enzyme which is without the hydrophobic region near the C-terminal of the native enzyme. Moreover, the present enzyme includes any protein containing an amino acid sequence within the first amino acid to the 614th amino acid and having the KEX2 endoprotease activity. Embodiments of the enzyme without the C-terminal hydrophobic region are those wherein 136 to 220 amino acid residues are deleted from the C-terminal region of the native enzyme.

To study in greater detail an ability of a soluble KEX2 endoprotease to be secreted extracellularly, the KEX2 activity is measured in a membrane fraction and a supernatant of a culture. For proteins having a C-terminal hydrophobic region such as expression products of KEX2(5.0) and KEX2Δ3 the activity thereof is mainly detected in a membrane fraction but little detected in a medium supernatant, and for proteins without a C-terminal hydrophobic region, such as expression products of KEX2 Δ5 and KEX2(RI-PvuII), the activity thereof is easily detected in a medium supernatant but is low in a membrane fraction, as seen in Table 3.

The above-mentioned results reveal that the hydrophobic region near the C-terminal is necessary for the binding to a membrane, and by deleting this hydrophobic region, the enzyme is able to be secreted in a medium. Moreover, from the comparison of the substrate specificities of a secreted calcium-dependent endoprotease activity and that in a membrane fraction from KEX2(5.0), it was found that the secreted calcium-dependent endoprotease activity exhibits a substrate specificity equal to the substrate specificity of the membrane enzyme. Therefore, the KEX2 endoproteases without the C-terminal hydrophobic region are soluble and maintain the properties of the native KEX2 endoprotease.

EXAMPLES

The present invention will now be further illustrated by but is by no means limited to the following examples.

Figure 3:
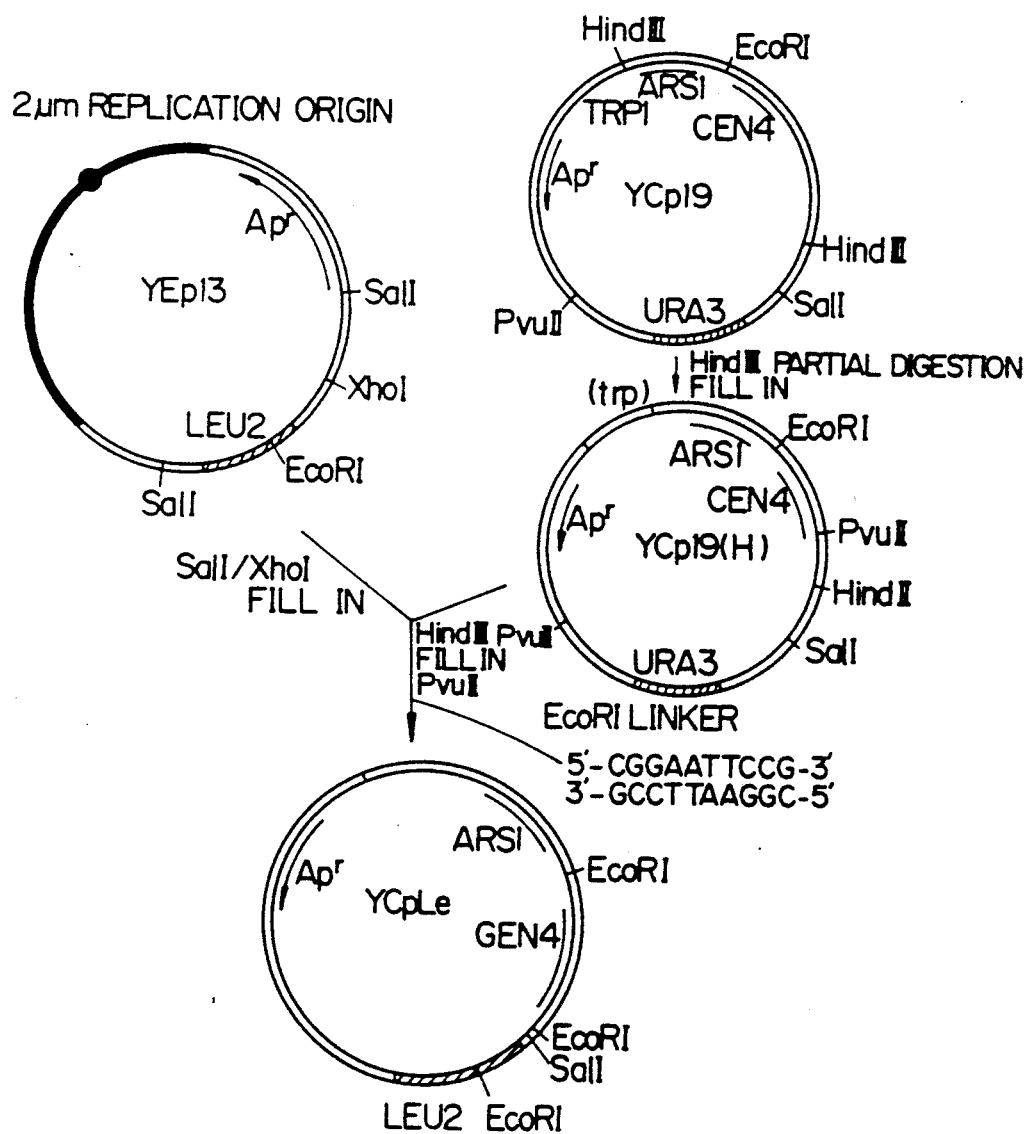

Example 1. Construction of pYE20 and YCpLe shuttle vector (FIGS. 2 and 3)

Plasmid pYE20 is an *E. coli*—yeast shuttle vector containing a 2 μm replication origin and a TRP1 gene derived from YRp7 as well as an ampicillin resistant gene and an origin of replication derived from pBR322, was constructed as follow.

Plasmid pYE2201 (Japanese Unexamined Patent Publication No. 61-56078) was cleaved with EcoRI, and cohesive ends of the resulting two DNA fragments were filled in using T4 DNA polymerase and 4 dNTPs, and the DNA fragments were ligated using DNA ligase to obtain pYE2201, The pYE2201, is a plasmid wherein the EcoRI site in pYE2210 has been deleted. In FIG. 2, the parenthesized EcoRI represents the deleted EcoRI site. Next, the pYE2201, was partially digested with SalI, and after filling in cohesive ends, religated to form pYE2202. The pYE2202 is a plasmid wherein one SalI site in pYE2201, has been deleted. In FIG. 2, the parenthesized Sal I represents the deleted Sal I. Plasmid pYE2202 was partially digested with HindIII and completely digested with SalI, and after filling in cohesive ends using T4 DNA polymerase and 4 dNTPs, a DNA fragment excluding the GAP-DH gene was obtained. This fragment was ligated via a 10 bp EcoRI linker (5'-CGGAATTCCG-3') to construct a plasmid pYE20.

YCpLe is an *E. coli*—yeast shuttle vector constructed by ligating ASR1 and a CEN 4 region derived from YCp19 (Stinchomb, D. T. et al., J. Mol. Biol., 158, 157–179, 1982) and LEU2 gene derived from YEp13 (Broach, J et al., Gene, 8, 121–133, 1979) with a DNA derived from pBR322 containing an ampicillin resistant gene and a replication origin. First, to inactivate the TRP1 gene present on YCp19, the YCp19 was partially digested with HindIII, and after filling in the resulting cohesive ends using a T4 DNA polymerase and 4 dNTPs, was religated to construct YCp19(H) wherein a HindIII site on the TRP1 gene has been deleted and TRP gene has been inactivated. Next, YCp19(H) was digested with HindIII and PvuII, and the resulting cohesive ends were filled in as described above to obtain a DNA fragment excluding the URA3 gene. On the other hand, YEp13 was cleaved with Xho I and Sal I, and the resulting cohesive ends were filled in as described above to obtain a 2.2 kb DNA fragment containing the LEU2 gene. Both fragments prepared as above and an EcoRI linker (5,-CGGAATTCCG-3,) were mixed and ligated to construct YCpLe (FIG. 3). The plasmids pYE20 and YCpLe thus obtained were used in Examples 2 and 4, respectively.

Example 2. Cloning of KEX2 cene

Chromosomal DNA of *Saccharomyces cerevisiae* X2180-1B (MATα SUC2 mal gal2 CUP1) was isolated by a method of Cryer et al., supra. Next, a 3.4 kb EcoRI fragment capable of complementing the kex2 mutation was isolated by a method of D. Julius, supra. Namely, the chromosomal DNA of *Sacch. cerevisiae* X2180-1B was digested with EcoRI, and the digested DNA fragments were separated by agarose gel electrophoresis. An agarose gel section containing DNA fragments of about 3.5 kb was cut off, and the DNA fragments were electroeluted, and precipitated with ethanol to recover the DNA fragments. On the other hand, the pYE20 obtained in Example 1 was cleaved with EcoRI to obtain a linearized pYE20 DNA. These DNA fragments were mixed and ligated with T4 DNA ligase, and the ligation mixture was used to transform *E. coli* DH-1. About 3000 clones separately obtained of ampicillin resistant transformants were mixed, and plasmids were isolated to prepare a gene bank (RI) of *Sacch. cerevisiae* X2180-1B chromosomal DNA.

Next, the gene bank was used to transform *Sacch. cerevisiae* K16-57C (MATα leu2 his3 ura3 trp1kex2-8) to obtain Trp+ transformants. From the transformants, strains producing a killer factor were selected using *Sacch. cerevisiae* 5X47 (MATa/MATα his1/+ trp1/+ ura3/+) as killer factor sensitive strain, by a method of Wicker and Leibowitz, supra. As a result, four killer factor producer strains were obtained from about 2000 Trp+ strains, and from thereamong, two transformants were used to isolate plasmid DNAs, which were then used to transform *E. coli* DH-1. From a resulting ampicillin resistant transformant, plasmid was isolated and designated as pYE-KEX2(RI)a. The pYE-KEX2(RI)a was used to transform *Sacch. cerevisiae* K16-57C to obtain Trp+ transformants, which were then examined to determine the killer factor productivity thereof. As a result, it was found that all the resulting transformants were killer factor producers. Accordingly, it was concluded that the pYE-KEX2(RI)a has a DNA fragment which complements the kex2-8 mutation.

Next, pYE-KEX2(RI)a was digested with EcoRI to obtain a 3.4 kb DNA fragment, which was then subcloned in pUC18. Resulting plasmid was analyzed using HindIII and BglII, and the same result as reported by D. Julius et al., supra, was obtained. The 3.4 kb DNA fragment complementing kex2-8 was cleaved with an adequate restriction enzyme such as NsiI, HindII, Sau-3AI, HaeIII, XbaI, BglII, Cfr101, ClaI, TagI, PvuII, or EcoRI, and each DNA fragments thus obtained was inserted to a multilinker site of M13mp18 or M13mp19 to determine a nucleotide sequence of the cloned DNA. As a result, although the cloned DNA contained a translation region coding for 715 amino acid residue, it did not have a stop codon. Therefore, isolation of a DNA fragment containing a downstream translation region was attempted. Namely, pYE-KEX2(RI)a was cleaved with BglII and SalI to obtain a larger DNA fragment. On the other hand, chromosomal DNA from *Sacch. cerevisiae* X2180-1B was digested with SalI and BglII to obtain DNA fragments of about 2.6 kb. These DNA fragments were mixed and ligated using T4 DNA ligase, and the ligation mixture was used to transform *E.* coli DH-1. About 3000 clones of separately obtained ampicillin resistant transformant were mixed, and plasmid DNAs were extracted to obtain a gene bank (5.0).

Figures 1, 4:
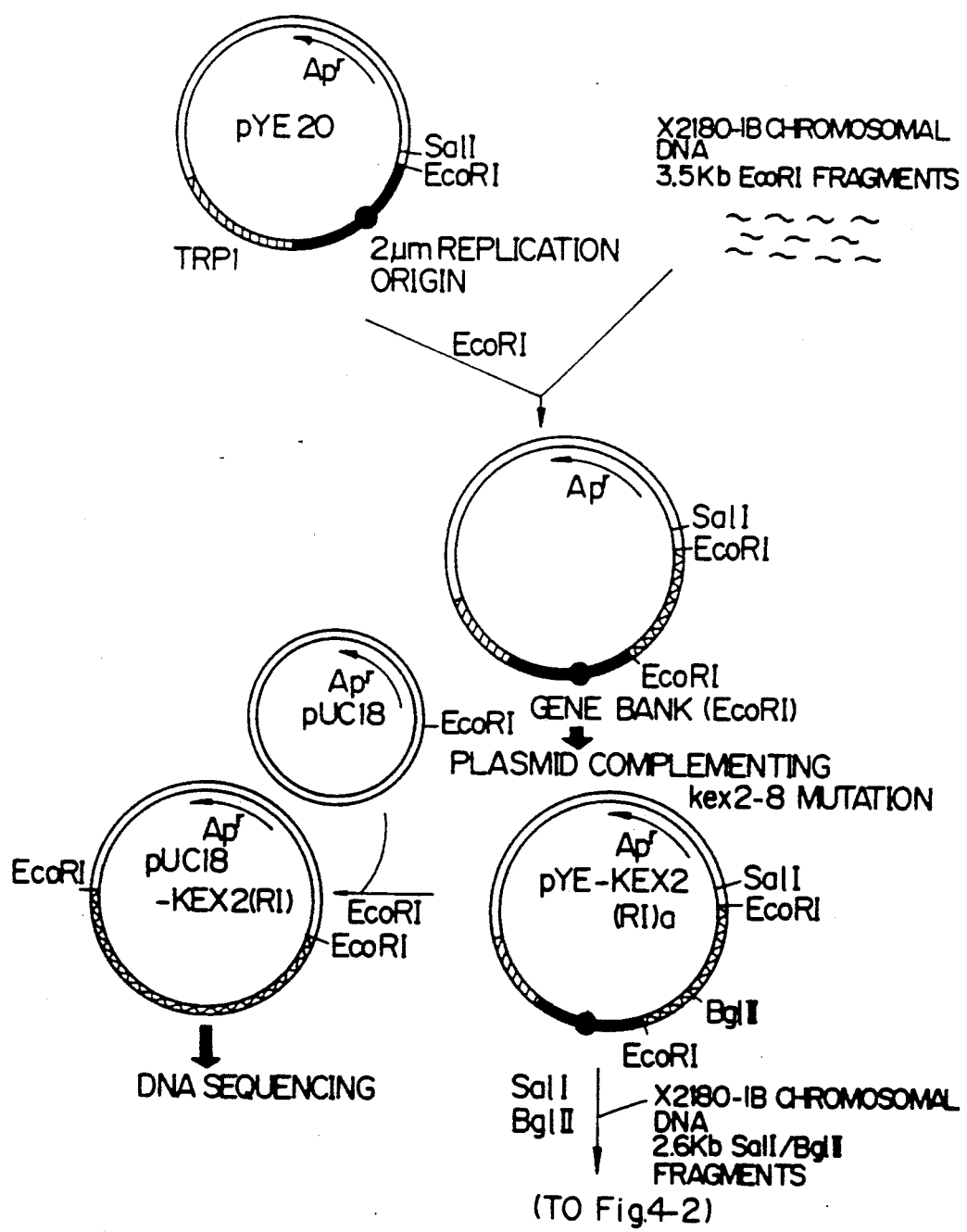
Figures 2, 4:
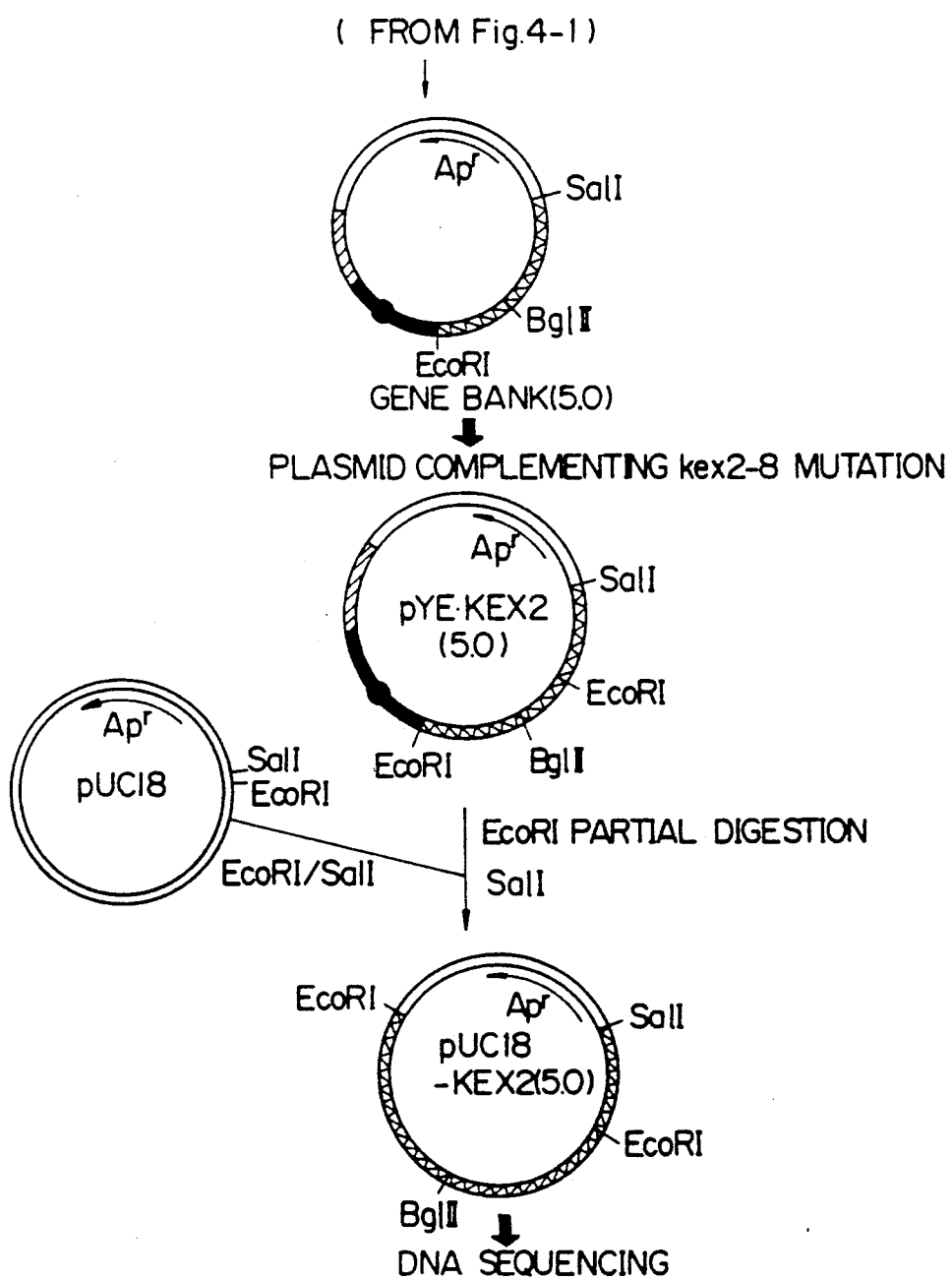

Next, this gene bank was used to obtain clones which complement a kex2-8 mutant by the procedure described above. As a result, five killer factor producing strains were obtained from about 2000 Trp+ transformants. From one strain thereamong, a plasmid DNA was recovered by the procedure described above. This plasmid was used to transform E. coli DH-1 to obtain an ampicillin resistant transformant. From the transformant, a plasmid was obtained and designated as pYE-KEX2(5.0). This plasmid was used to transform Sacch. cerevisiae, and all of the Trp+ transformant had a killer factor producing ability. Plasmid pYE-KEX2(5.0) was digested partially with EcoRI and completely with Sal I to obtain a 5.0 kb DNA fragment. This fragment was inserted between the EcoRI and Sal I sites of pUC18 to obtain pUC18-KEX2(5.0) (FIG. 4). The nucleotide sequence of the DNA fragment was determined by the procedure described above, and it was found that the DNA fragment contains an entire translation region coding for 814 amino acids. Note, E. coli DH-1 transformed with pUC18-KEX2(5.0) was designated as Escherichia coli SBM298, and deposited with the Fermentation Research Institute Agency of Industrial Science and Technology (FRI), 1-3, Higashi 1 chome, Tsukuba-shi, Ibaraki, Japan, as FERM P-9796 on Dec. 28, 1987, and transferred to a deposition under the Budapest treaty as FERM BP-2194 on Dec. 16, 1988.

Example 3. Assay of protease activity

Yeast cells were cultured in a medium containing 1% casamino acid, 0.7% Yeast Nitrogen Base W/O amino acid (Difco), 2% dextrose, and 30 µg/ml uracil at 30° C.

hours, and the culture broth was centrifuged to obtain cells. For the assay of intracellular protease activity, the cells were treated to prepare "permeabilized cells" using a surfactant Brij 58 by a method of D. Julius et al., supra. Enzyme activity was measured by a method of K. Mizuno et al., BBRC, 144, 807–814, 1987. Briefly, a sample was reacted with 20 nmoles of Boc-Gln-Arg-Arg-MCA as a substrate in 250 µl of a reaction mixture containing 0.4 M Tris-HCl (pH 7.0), 0.1% lubrol, 1 mM EDTA, 1 mg/ml pepstatin and 1 mg/ml bestatin in the presence or absence of 2 mM $CaCl_2$ at 37° C. for one hour, and the fluorescence intensity at 460 nm was measured at a 380 nm excitation on a spectrophotofluorometer. An increase of the fluorescence intensity by the addition of $CaCl_2$ was a measure of the KEX2 endoprotease activity.

Example 4. KEX2 endoprotease activity and ability to complement kex2-8 mutation of various plasmids The plasmids pYE-KEX2(RI)a and pYE-KEX2(5.0) are both multicopy plasmids in yeast cells in virtue of 2 µm replicon. Therefore, to study the protease activity and the ability to complement a kex2-8 mutation in a single copy plasmid, YCp-type plasmids were constructed as follows.

Figure 8:
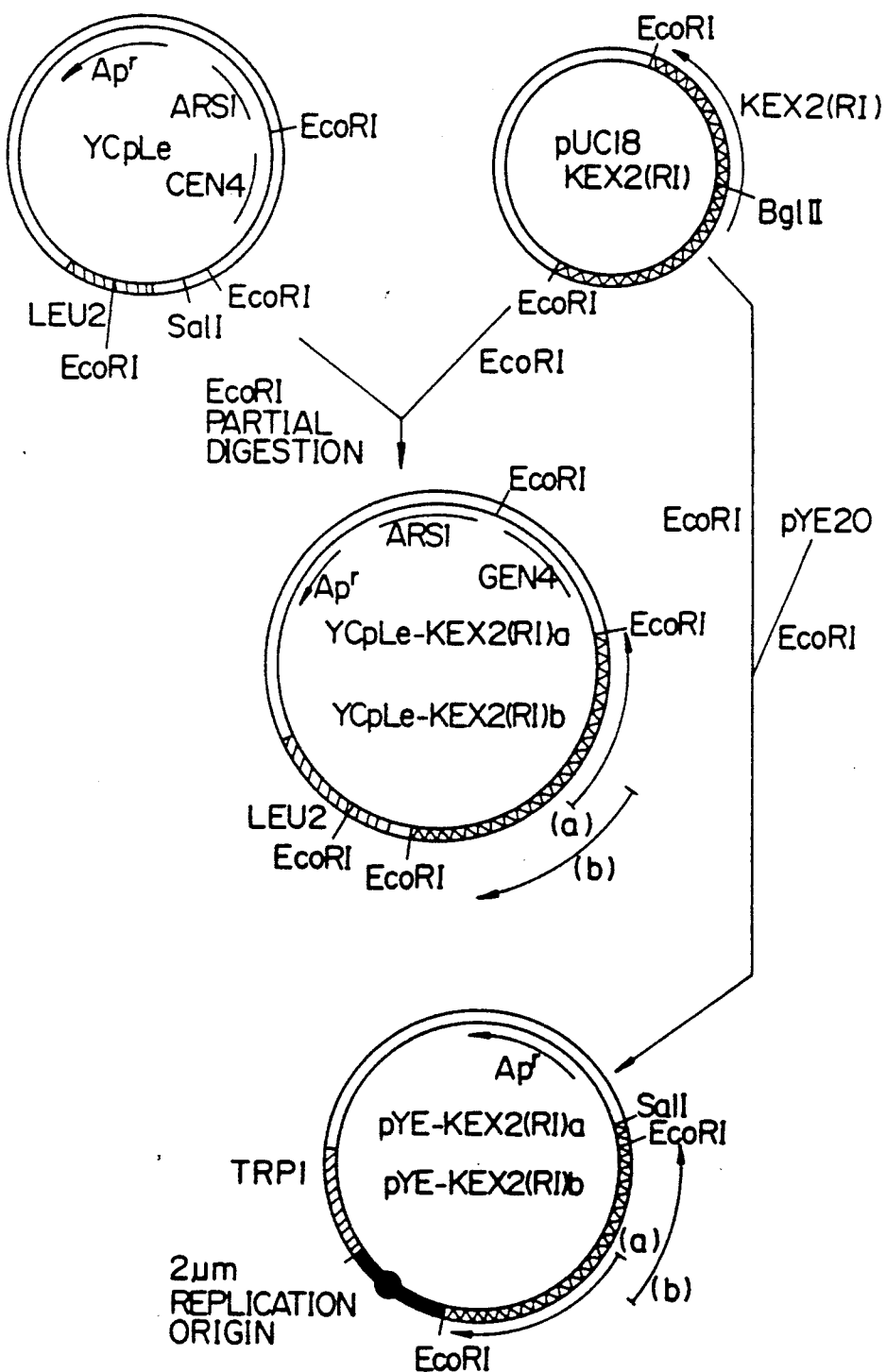
FIG. 8 represents a process for the construction of YCpLe-KEX2(RI)a, YCpLe-KEX2(RI)b, pYE-KEX-2(RI)a, and pYE-KEX2(RI)b, wherein (a) and (b) show the directions of insertion of the KEX2 gene.

The YCpLe constructed in Example 1 was partially digested with EcoRI to linearize the plasmid, and pUC18-KEX2 (RI) was digested with EcoRI to obtain a 3.4 kb DNA fragment containing the KEX2 gene. These DNA fragments were mixed and ligated to form YCpLe-KEX2(RI)a and YCpLe-KEX2(RI)b, wherein the directions of the inserted 3.4 kb DNA fragment to the former and latter plasmids are different, (FIG. 8). Moreover, the 3.4 kb DNA fragment was inserted into the EcoRI site of pYE20 to construct pYE-KEX2(RI)a and pYE-KEX2(RI)b wherein the directions of the 3.4 kb DNA fragment inserted to the former and latter plasmids are different, (FIG. 8). Note, pYE-KEX2(RI)a in FIG. 8 is the same as pYE-KEX2(RI)a in FIG. 4.

The above-obtained four plasmids and plasmid pYE-KEX2(5.0) constructed in Example 2 were separately used to transform a Sacch. cerevisiae K16-57C kex2-8 mutant. The ability to complement the kex2-8 mutation of the resulting LEU+ or TRP+ transformants was examined, using a killer productivity as the indicator. The results are shown in Table 1.

TABLE 1

| Sac. cerevisiae strain | Direction of inserted KEX2 gene | | Killer activity | Endoprotease activity |
|---|---|---|---|---|
| K16-57C (non) | — | | — | 0.5 |
| K16-57C [pYE-KEX2(RI)a] | ——KEX2(RI)——> | IRI | + | 22.9 |
| K16-57C [pYE-KEX2(RI)b] | <——KEX2(RI)—— | IRI | ++ | 50.3 |
| K16-57C [pYE-KEX2(5.0)] | <——KEX2(5.0)—— | IRI | ++ | 78.8 |
| K16-57C [YCpLe-KEX2(RI)a] | ——KEX2(RI)——> | CEN4 | + | 5.0 |
| K16-57C [YCpLE-KEX2(RI)b] | <——KEX2(RI)—— | CEN4 | + | 11.1 |
| R27-7C (non) | — | | + | 7.2 |

As seen from Table 1, all five plasmids used herein complemented the kex2 mutation, thus revealing an ability to produce the killer factor. The killer productivity of transformants with pYE-KEX2(RI)b and pYE-KEX2(5.0) is higher than with the others, and a host that was not transformed did not exhibit the killer productivity. Note, Sacch. cerevisiae R27-7C is a killer producer.

Further, the enzyme activity was measured by the procedure described above, and it was found that all of the five transformants exhibited a KEX2 endoprotease activity more than the times higher than that of the host alone, wherein the KEX2 gene had been mutated, which exhibited the enzyme activity of 0.5. The above-mentioned two transformants, which exhibited a higher killer activity, also exhibited a higher enzyme activity. Transformants with a YEp-type vector exhibited a higher enzyme activity than that exhibited by transformants with a YCp-type vector, probably due to the gene dosage effect provided by multicopying.

Although pYE-KEX2(RI)a and pYE-KEX2(RI)b comprises a KEX2 gene coding for a KEX2 endoprotease without the C-terminal portion of the native KEX2 endoprotease, both plasmids provided the activities regardless of the direction of insertion of the gene. This strongly suggests that the C-terminal portion of the native KEX2 endoprotease is not important, in so far as its biological activities are considered.

Figure 9:
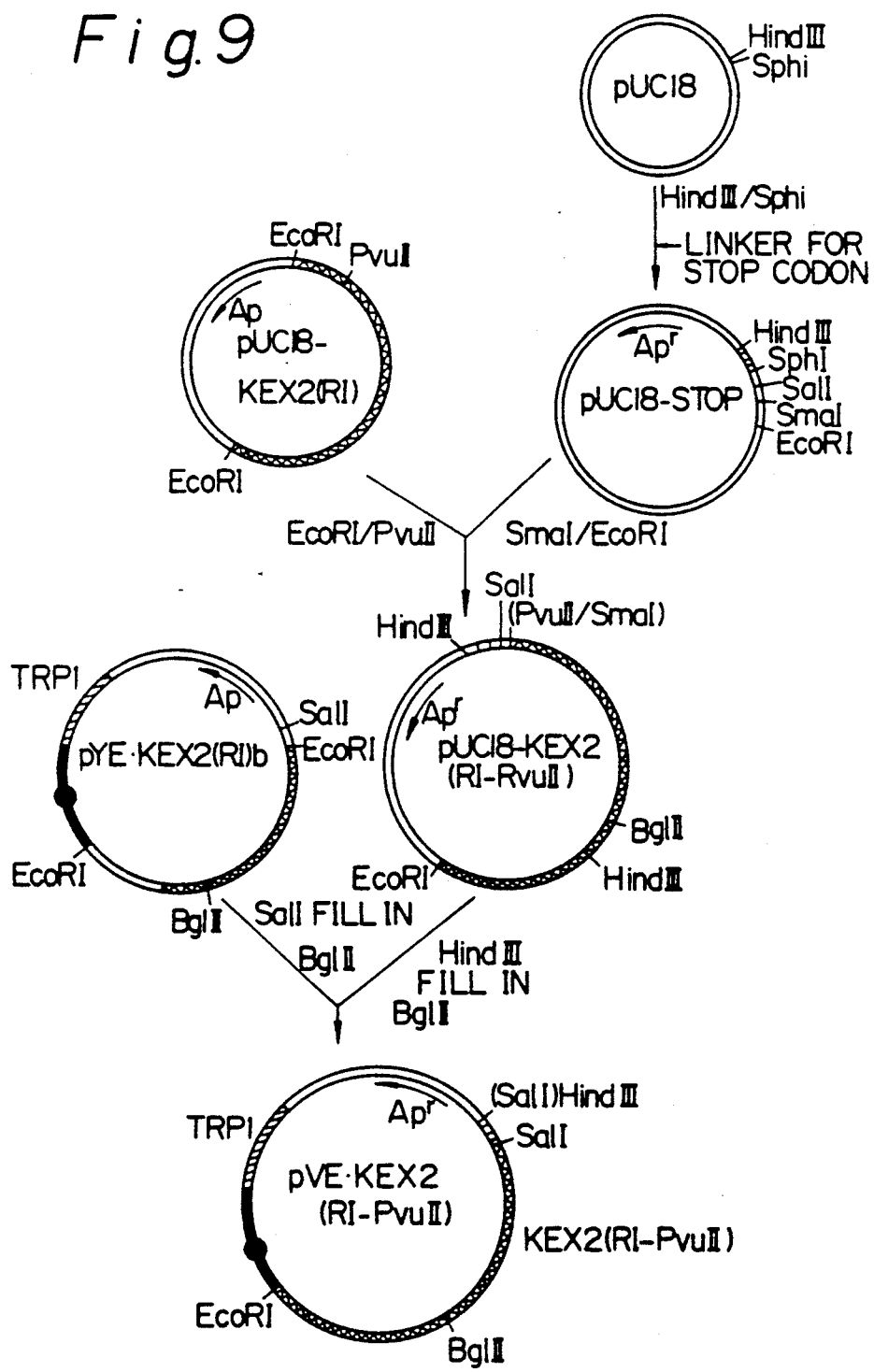
FIG. 9 represents a process for the construction of pYE-KEX2(RI-Pvu II)
Figure 10:
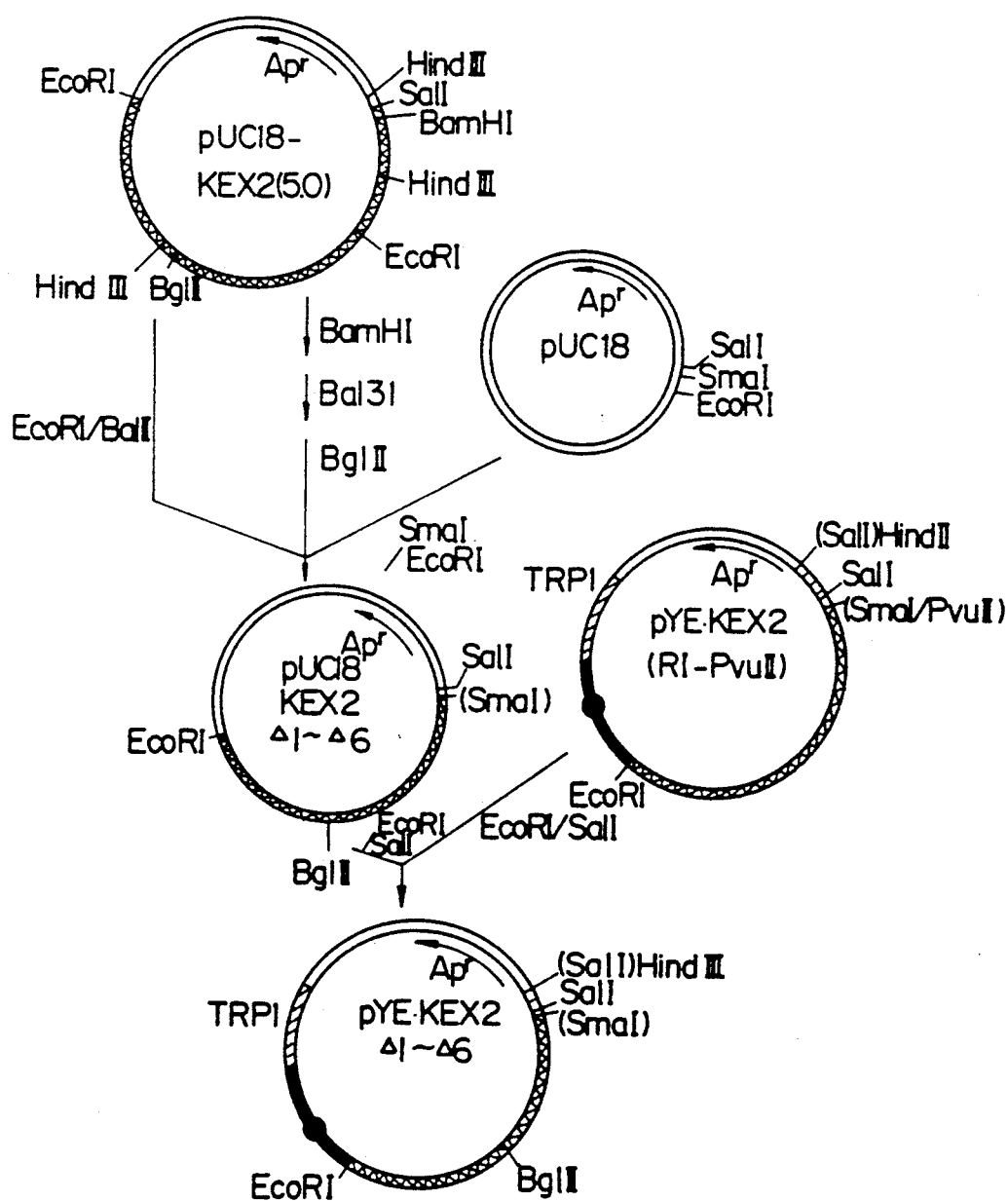
FIG. 10 represents a process for the construction of pYE-KEX2 Δ1 to pYE-KEX2 Δ6.

Example 5. Construction of KEX2 genes coding for enzyme lacking C-terminal portion (FIGS. 9 and 10)

To confirm that C-terminal portion is not important to the biological activity, various plasmids comprising KEX2 gene coding for KEX2 endoprotease without the C-terminal portion of the native enzyme, to different extents, were constructed.

To this end, a new stop codon must be introduced, and accordingly, a plasmid pUC18-STOP was constructed by inserting a synthetic stop codon linker between the HindIII and SphI sites of pUC18. Namely, the following synthetic linker:

```
5' CTTAATTAATTAAGCA      3'
3' GTACGAATTAATTAATTCGTTCGA 5'
    (SphI)              (HindIII)
``` was prepared by a conventional procedure for chemically synthesizing a oligonucleotide. On the other hand, plasmid pUC18 was digested with HindIII and SphI, and the linearized pUC18 and the above-mentioned synthetic linker were mixed and ligated using T4 DNA ligase to construct pUC18-STOP.

Next, pUC18-KEX2(RI) was digested with EcoRI and Pvu II to obtain a 3.1 kb DNA fragment containing the KEX2 gene, and pUC18-STOP was digested with SmaI and EcoRI to obtain a 2.6 kb DNA fragment. The above-prepared two DNA fragments were ligated using T4 DNA ligase to construct pUC18-KEX2(RI-PvuII). The plasmid pUC18-KEX2 was digested with HindIII, the resulting cohesive ends were filled in using T4 DNA polymerase and 4 dNTPs, and the DNA fragment was cleaved with BglII to obtain an 0.8 kb DNA fragment. On the other hand, pYE-KEX2(RI)b was digested with SalI, the resulting cohesive ends were filled in as described above, and the resulting DNA fragment was cleaved with BglII to obtain a DNA fragment containing the TRP1 gene. The above-prepared two DNA fragments were ligated to construct pYE-KEX2(RI-PvuII). The KEX2 gene in the pYE-KEX2-(RI-PvuII) does not contain a 0.6 kb region of the 3'-terminal side, and codes for a KEX2 endoprotease without the C-terminal hydrophobic region.

Next, various plasmids comprising the KEX2 gene coding for the KEX2 endoprotease without the C-terminal portion of the native enzyme, to different extends, were constructed. Namely, pUC18-KEX2(5.0) was cleaved with BamHI, and the linearized plasmid was shortened by Bal 31 exonuclease digestion and cleaved with BglII. The reaction mixture was subjected to agar gel electrophoresis to obtain DNA fragments having different lengths of 0.5 kb to 1.4 kb. Further, pUC18-KEX2(5.0) was digested with EcoRI and Bgl II to obtain a 2.3 kb DNA containing a KEX2 gene coding for an N-terminal portion of the KEX2 endoprotease, pUC18 was cleaved with EcoRI and SmaI to obtain a linearized pUC18 vector. The above-prepared three components were mixed and ligated using T4 DNA ligase, to construct plasmids pUC18KEX2Δ1 to pUC18KEX2Δ6 each containing a KEX2 gene without a 3'-portion of the native gene, to a different extent.

Next, each plasmid pUC18KEX2Δ1 to Δ6 was cleaved with EcoRI and SalI to obtain a DNA fragment containing the shortened KEX2 gene, and plasmid pYE-KEX2(RI-PvuII) was digested with EcoRI and SalI to obtain a DNA fragment not containing the KEX2 gene. The above-prepared two DNA fragments were ligated to construct pYE-KEX2Δ1, pYE-KEX2Δ2, pYE-KEX2Δ3, pYE-KEX2Δ4, pYE-KEX2Δ5, or pYE-KEX2Δ6, respectively, depending on the parent plasmids pUC18KEX2Δ1 to pUC18KEX2Δ6. The above-mentioned pYE-type plasmids contained a deletion of 1.0 kb, 0.8 kb, 0.2 kb, 0.3 kb, 0.65 kb and 0.75 kb, respectively, in comparison to the native KEX2 gene. In the above-mentioned PYE-type plasmids, the 3'-terminal of the shortened KEX2 gene is followed by a stop codon derived from pUC18-STOP.

Example 6. Assay of biological activities of C-terminal-shortened KEX2 enzyme

Plasmids pYE-KEX2(5.0) constructed in Example 2, pYE-KEX2(RI)b constructed in Example 4, and pYE-KEX2Δ1 to pYE-KEX2Δ6 and pYE-KEX2(RI-PvuII) constructed in Example 5, were separately used to transform Sacch. cerevisiae K16-57C (kex2-8 mutant) to obtain corresponding yeast transformants. An evaluation was made of each transformant, to determine the ability thereof to complement a kex2 mutation, by the same procedure described in Example 2, and to determine the endoprotease activity thereof by the same procedure described in Example 3. The results are shown in Table 2.

TABLE 2

| Plasmid | Hind III / Bgl II / Pvu II / EcoRI / Hind III map | Killer activity | Endoprotease activity Exp1 | Exp2 |
|---|---|---|---|---|
| pYE-KEX2(RI)b |  ---> | ++ | 85.1 | 73.1 |
| pYE-KEX2(5.0) | ────────────────────────> | ++ | 121.0 | 258.3 |

TABLE 2-continued

| Plasmid | Hind III — Bgl II — Pvu II — EcoRI — Hind III | Killer activity | Endoprotease activity Exp1 | Endoprotease activity Exp2 |
|---|---|---|---|---|
| pYE-KEX2Δ3 | ———————————→ | ++ | 87.0 | 114.4 |
| pYE-KEX2Δ4 | ——————————→ | ++ | 88.6 | 61.4 |
| pYE-KEX2(RI-PvuII) | —————————→ | + | 162.0 | 207.3 |
| pYE-KEX2Δ5 | ————————→ | + | — | 264.0 |
| pYE-KEX2Δ6 | ———————→ | — | — | 0 |
| pYE-KEX2Δ2 | ——————→ | — | 2.4 | 0 |
| pYE-KEX2Δ1 | —————→ | — | 3.0 | 0 |

1*: All products start from the first amino acid in FIG. 1. Parenthesized numbers denote the number of the C-terminal amino acid.

As seen from Table 2, expression products encoded by a KEX2 gene shortened at the 3,-terminal thereof of an extent of less than 0.65 kb, exhibit the endoprotease activity, but expression products encoded by a KEX2 gene shortened at the 3,-terminal thereof to an extent of more than 0.65 kb do not exhibit the enzyme activity. The ability to complement a kex2 mutation is satisfactorily correlated to the enzyme activity. Namely, the transformants transformed with a plasmid comprising a KEX2 gene shortened at the 3,-terminal thereof to an extent of more than 0.65 kb (about 220 amino acids) do not complement the kex2 mutation of the host.

Example 7. Extracellular secretion of expression product

To evaluate the possibility of a secretion of expression products from plasmids pYE-KEX2(5.0), pYE-KEX2Δ2, pYE-KEX2Δ3, pYE-KEX2Δ5, and pYE-KEX2 (RI-Pvu II), each plasmid was used to transform *Sacch. cerevisiae* K16-57C, and the transformant was cultured by the procedure described in Example 2, and the culture broth was centrifuged to separate a supernatant and cells. The supernatant was 15-fold concentrated using Centricon (Amicon) to obtain a sample for an assay of the enzyme activity in the supernatant. On the other hand, the cells were suspended in 0.1 M Tris-HCl, and disrupted using glass heads. The disruptant was centrifuged at 2,000 rpm for one mixture, to precipitate the glass beads and intact cells. The resulting supernatant was centrifuged at 15,000 rpm for five minutes to obtain a precipitate, which was then dissolved in 0.1% lubrol. This solution was used as a sample for an assay of the enzyme activity in the membrane fraction. The results are shown in Table 3.

TABLE 3

| Plasmid | Size of expression product (N-terminal hydrophobic region — Region homologous with subtilisin — C-terminal hydrophobic region) | Endoprotease activity Membrane fraction | Endoprotease activity Supernatant |
|---|---|---|---|
| pYE-KEX2(5.0) | full length | 21.6 | 0.1 |
| pYE-KEX2Δ2 | truncated (no subtilisin region complete) | 0.0 | 0.0 |
| pYE-KEX2Δ3 | truncated after subtilisin region | 5.3 | 0.5 |
| pYE-KEX2Δ5 | extended further | 0.4 | 4.0 |
| pYE-KEX2(RI-PvuII) | extended further | 0.1 | 5.6 |

As seen from Table 3, for transformants with pYE-KEX2Δ5 and pYE-KEX2(RI-PvuII), the membrane fraction did not exhibit the endoprotease activity, but the supernatant exhibited the enzyme activity. On the other hand, for transformants with pYE-KEX2(5.0) and pYE-KEX2Δ3, the membrane fraction exhibited the enzyme activity, but the supernatant did not. For transformants with pYE-KEX2Δ2, neither the supernatant nor membrane fraction exhibited the enzyme activity, which result confirms satisfactorily with the result shown in Table 2.

The above result shows that the KEX2 product without the C-terminal hydrophobic region can be secreted in a culture medium, suggesting that the C-terminal hydrophobic region is responsible for the binding of the KEX2 endoprotease to a membrane structure such as a Golgi body in a cell.

Example 8. Substrate specificity of soluble KEX2 endoprotease

To compare the substrate specificity of the soluble KEX2 endoprotease and the native KEX2 endoprotease, concentrated supernatants from culture of transformants with pKEX2(RI-PvuII) or pKEX2Δ5 and a membrane fraction from cells of a transformant with pKEX2(5.0) were tested to determine the enzyme activity to various substrates thereof. Note, the used supernatant and membrane fraction were prepared as described in Example 7. The results are shown in Table 4.

TABLE 4

| Substrate | Relative activity | | |
|---|---|---|---|
| | KEX2(5.0)* | KEX2(RI-Pvu II)** | KEX2 Δ5** |
| Boc—Gln—Arg—Arg—MCA | 100% | 100% | 100% |
| Boc—Leu—Arg—Arg—MCA | 100% | 124% | 112% |
| Boc—Leu—Lys—Arg—MCA | 82% | 87% | 94% |
| Boc—Val—Pro—Arg—MCA | 36% | 44% | 41% |
| Boc—Glu—Lys—Lys—MCA | <0.2% | <0.3% | <0.5% |
| Z—Phe—Arg—MCA | <0.2% | <0.3% | <0.5% |
| Arg—MCA | <0.2% | <0.3% | <0.5% |

*Membrane fraction, i.e., insoluble fraction from disrupted cells.
**Concentrated supernatant from culture broth.

Relative activities for various substrates are shown in relation to an activity of each enzyme preparation to a substrate Boc-Gln-Arg-Arg-MCA as 100%. The results shown in Table 4 make it clear that soluble enzymes secreted in a medium, i.e., KEX2(RI-Pvu II) and KEX2Δ5 have substantially the same substrate specificity as that of a membrane fraction, i.e., KEX2(5.0). Namely, a soluble KEX2 endoprotease without the C-terminal hydrophobic region exhibits the same substrate specificity as the native KEX2 endoprotease.

As described above, according to the present invention, a KEX2 endoprotease, both the native type and the soluble type without the C-terminal hydrophobic region, can be easily and industrially produced in a large amount, and since the soluble type enzyme is secreted in a culture medium, purification thereof is very easy. The present KEX2 endoprotease can be used to prepare various kinds of biologically active polypeptides or protein, the activation of which requires a post-translational processing.

We claim:

1. A KEX2 endoprotease without a C-terminal hydrophobic region and having an amino acid sequence from the first N-terminal amino acid to an amino acid selected from the group consisting of the 594th up to and including the 614th amino acid shown in FIG. 1.

2. A KEX2 endoprotease consisting of an amino acid sequence from the first amino acid to the 594th amino acid shown in FIG. 1.

* * * * *